United States Patent [19]

Taratuta et al.

[11] Patent Number: 5,072,731
[45] Date of Patent: Dec. 17, 1991

[54] APPARATUS FOR DETECTING CATARACTOGENESIS USING QUASIELASTIC LIGHT SCATTERING

[75] Inventors: Victor G. Taratuta, Boston; George M. Thurston; George B. Benedek, both of Belmont, all of Mass.

[73] Assignee: Massachusetts Institute of Technology, Cambridge, Mass.

[21] Appl. No.: 583,777

[22] Filed: Sep. 17, 1990

Related U.S. Application Data

[60] Division of Ser. No. 463,883, Jan. 8, 1990, Pat. No. 4,957,113, which is a continuation of Ser. No. 91,658, Sep. 1, 1987, abandoned.

[51] Int. Cl.⁵ .............................................. A61B 3/10
[52] U.S. Cl. .................................... 128/633; 128/665; 128/745
[58] Field of Search ............... 128/633, 664, 665, 745, 128/666

[56] References Cited

U.S. PATENT DOCUMENTS

4,702,576  10/1987  Magnante ............................ 128/745
4,711,542  12/1987  Ichihashi ............................ 351/221

Primary Examiner—Kyle L. Howell
Assistant Examiner—Robert L. Nasser, Jr.
Attorney, Agent, or Firm—Seed and Berry

[57] ABSTRACT

An apparatus is disclosed for using quasielastic light scattering to determine the degree of cataractogenesis of a lens in vivo. By collecting and analyzing light scattered from the lens, it is possible, using the autocorrelation function or the power spectrum, to separate the fluctuations into two components: one caused by fast diffusing proteins and one caused by slow diffusing protein aggregates. This data may be applied to an experimentally determined and theoretically deduced universal curve in order to determine quantitatively the degree of cataractogenesis at that particular location in the lens.

59 Claims, 4 Drawing Sheets

APPARATUS FOR DETECTING CATARACTOGENESIS USING QUASIELASTIC LIGHT SCATTERING

GOVERNMENT SUPPORT

The invention described herein was supported in whole or in part by a grant from the National Institutes of Health.

CROSS-REFERENCE TO RELATED APPLICATION

This application is a divisional of U.S. application Ser. No. 07/463,883 filed Jan. 8, 1990, now U.S. Pat. No. 4,957,113 patented Sept. 18, 1990. which is a continuation of U.S. application Ser. No. 07/091,658 filed Sept. 1, 1987, now abandoned.

BACKGROUND OF THE INVENTION

A reliable, quantitative and non-invasive method for the characterization of the molecular changes associated with early cataractogenesis in-vivo has long been an important goal of human clinical cataract research. Such a method would allow researchers and physicians to: a) assess the effectiveness of putative anticataract reagents; b) evaluate the cataractogenic role of pharmacologic agents or radiation used in the treatment of systematic disease; c) characterize early cataract in epidemiologic studies of human or animal populations subject to differential cataractogenic stress; and, d) provide a quantitative basis for the medical decision to intervene surgically or pharmaceutically in the treatment of cataract.

In 1975, T. Tanaka and G. Benedek, ("Observation of Protein Diffusivity in Intact Human and Bovine Lenses with Application to Cataract," Invest. Ophthal. 14, 449-456 (1975).) showed that the Brownian motion of proteins in excised human and bovine lenses could be measured optically using the method of quasielastic light scattering spectroscopy. Following this work, T. Tanaka and C. Ishimoto, ("In Vivo Observation of Protein Diffusivity in Rabbit Lenses," Invest. Opthal. and Vis. Sci. 16, 135-140 (1977).) demonstrated in 1977 that it was possible to conduct quasielastic light scattering measurements safely in the lens of the eye of a living rabbit.

In 1984, Nishio et al., ("In Vivo Observation of Lens Protein Diffusivity in Normal and X-Irradiated Rabbit Lenses, Exp. Eye Res. 39, 61-68 (1984).) demonstrated that quasielastic light scattering could be used in vivo in the rabbit to detect changes in mean protein diffusivity as a function of position and age in the lens. Further observations showed that the cataractogenic insult of X-irradiation upon the rabbit lens produced dramatic changes in the form of the autocorrelation function of the scattered light at a very early stage in the cataractogenic process. This change in the autocorrelation function, the mathematical heart of quasielastic light scattering analysis, demonstrated that the X-irradiation was responsible for drastic changes in the diffusivity of the protein scattering elements undergoing Brownian movement within the ocular tissue. Both Nishio and the 1977 Tanaka team observed that these altered correlation functions had a form different from that expected for the Brownian motions of a single type scatterer. However, neither undertook a quantitative analysis of the information contained in the non-exponential character of the autocorrelation function observed.

In 1986, T. Libondi et al., ("In Vivo Measurement of the Aging Rabbit Lens Using Quasielastic Light Gathering," Curr. Eye Res., Vol. 5, 6, 411-419 (1986).) showed that the form of the autocorrelation function of the scattered light from a living rabbit eye indicated the presence of at least two distinct diffusing species within the rabbit lens. One species had a diffusivity corresponding to the α-crystalline protein. The other was a much more slowly diffusing species of the type discovered in-vitro by M. Delaye et al., ("Identification of the Scattering Elements Responsible for Lens Opacification in Cold Cataracts," Biophys. J. 37, 647-656 (1982).) in 1982.

SUMMARY OF THE INVENTION

The present invention provides a method for non-invasive in-vivo inspection of ocular tissue. More specifically, a laser is used to provide a low power, coherent and uniform beam of light which is guided through an optical system to the eye of a subject for scattering by protein molecules in the ocular tissue of the subject. The scattered light is viewed and collected by another optical system. This collected light is applied to a square law detector whose output current contains fluctuations associated with the Brownian movement of the scattering molecules. It is possible to mathematically analyze the current fluctuations so as to associate them with particular protein groups. By determining the relative intensity of light scattered from each group, it is possible to accurately and quantitatively estimate the degree of cataractogenesis occurring in that location of ocular tissue.

Thus, the present invention pertains to a method for in-vivo inspection of ocular tissue comprising:
 (a) providing a source of substantially monochromatic, coherent, collimated light;
 (b) focusing light from the source on a specific measurement location of a subject's ocular tissue;
 (c) collecting the light scattered by the ocular tissue;
 (d) converting the scattered light using an optical square law detector into an electrical signal representative of temporal fluctuations in the intensity of the scattered light;
 (e) analyzing the electrical signal produced by the scattered light to determine the relative average intensity of the light scattered by slow moving protein aggregates in the ocular tissue ($I_s$) and the relative average intensity of the light scattered by fast moving protein species in the ocular tissue ($I_f$);
 (f) using the determined values of $I_s$, $I_f$ and their sum ($I_{tot}$) to produce a universal curve; and,
 (g) using the determined values of $I_s$ and $I_f$ to locate a position on the universal curve which corresponds to the degree of cataractogenesis at the specific measurement location in the ocular tissue of the subject.

The method for in-vivo inspection of ocular tissue described herein has a number of advantages over currently known techniques for determining the degree of cataractogenesis. Unlike the present method, visual observation of the eye lens using a slit lamp microscope is not a quantative method, nor is it sensitive enough to detect the earliest changes in scattered light produced by the first stages of cataract formation. Current photographic methods are useful for characterizing later stages of cataractogenesis. However, the instrumentation is expensive and insensitive to early cataractogenic changes due to the logarithmic response of photographic film.

The above and other features of the invention including various novel details of combination of parts will now be more particularly described and pointed out in the claims. It will be understood that the particular cataractogenesis detection method embodying the invention is shown by way of illustration only and not as a limitation of the invention. The principles and features of this invention may be employed in various and numerous embodiments without departing from the scope of the invention.

DETAILED DESCRIPTION OF THE INVENTION

The proteins present in ocular tissue undergo random diffusive movement due to continuous collisions with nearby molecules. When a coherent, steady beam of light is scattered by the moving proteins, the intensity of the scattered light fluctuates in time. The movements of the proteins determine the rate of intensity fluctuation. As it has been determined that small proteins generally diffuse faster than larger proteins or protein aggregates, it is possible to examine the detector current fluctuations to determine the relative intensity of light scattered from the small protein species and the large protein species within the lens tissue, and to determine as well the relative amounts of these two species and their individual diffusivities.

The aggregation of small proteins within the lens is the very first stage in the process of cataractogenesis. By using information obtained from the light scattered by the various fast and slow moving protein species, it is now possible to interpret, in a clear and unambiguous manner, the meaning of the components contained in the autocorrelation function or the power spectrum. This information may be used to generate an algorithm which provides a universal curve for cataract development. By locating the position on this curve corresponding to each selected position in the lens, it is possible to characterize in a very simple manner the precise degree of cataractogenesis occurring at that selected point in the lens. In effect, this invention permits the decoding of the information contained in the random intensity fluctuations in the light scattered from the lens. When placed on the disclosed universal curve, the decoded information has been shown clinically to provide an accurate quantitative measure of cataract development on a molecular level long before it could be detected visually by either the subject or the physician.

Brownian motion is defined as the motion of macromolecules caused by thermal agitation and the random striking by neighboring molecules in a solution. In the lens of the human eye, protein molecules undergoing Brownian motion may be recorded and analyzed by quasielastic light scattering.

In quasielastic light scattering (QLS), the temporal fluctuations in intensity of light scattered by a selected small volume in the lens which is illuminated by an incident laser beam are studied. The scattered light intensity fluctuates in time because of the Brownian motion of the scattering elements. In the case in which the laser beam illuminates the lens of the eye, the scattering elements are the molecular constituents of the fiber cells within the lens. These constituents are principally globular proteins called crystallins.

The light intensity fluctuations are detected by collecting the light scattered from a well-defined, illuminated volume in the eye lens and focussing this light onto the surface of an optical square law detector such as a photomultiplier tube or solid-state photodiode. The output of the detector is a photo-electric current whose temporal fluctuations are in synchrony with the fluctuations in the scattered light intensity. The temporal fluctuation in the photocurrent can be analyzed mathematically by obtaining the autocorrelation function or the power spectrum of the photocurrent. From the mathematical form of the autocorrelation function or the power spectrum of the photocurrent, it is possible to determine the diffusivity of the scattering elements undergoing Brownian movement.

The autocorrelation function may be determined by using an autocorrelator to analyze the fluctuations in the intensity of the laser light scattered by the ocular tissue. Correspondingly, the power spectrum may be determined using a spectrum analyzer. The random motions of the crystalline proteins within the lens give rise to concentration fluctuations, which in turn give rise to fluctuations in the intensity of the scattered light. This scattered light may be recorded in the form of a time correlation function, the autocorrelation function $G(\tau)$, which relates the scattered light intensity at a time t, I(t), to that a certain time $\tau$ later, I (t + $\tau$), as follows:

$$G(\tau) = <I(t)I(t+\tau)>$$

where $<>$ denoted averaging over all starting times t.

The photocurrent correlation function will have a form which in first order can be expressed as consisting of two exponential functions:

$$G(\tau) = (I_f + I_s)^2 + a(I_f e^{-\Gamma_f \tau} + I_s e^{-\Gamma_s \tau})^2. \quad (1)$$

In this equation, $I_f$ is the intensity of light scattered from the fast diffusing protein species within the ocular tissue and $I_s$ is the intensity of light scattered from the slow diffusing protein species in the ocular tissue. $\Gamma_f = D_f K^2$ is the decay rate of the fast diffusing species and $\Gamma_s = D_s K^2$ is the decay rate of the slow diffusing species. $D_f$ and $D_s$ are the diffusivities of the fast and slow species respectively. $K = (4\pi n/\lambda) \sin (\theta/2)$ is the scattering vector where n = index of refraction of the lens; $\lambda$ = wavelength of the laser in vacuo; and $\theta$ = scattering angle. Additionally $a = (\frac{1}{2}N)$ where N = number of coherence areas in the exit aperture of the collection optics.

The first step in the analysis is to take the experimental measurements of $G(\tau)$ and to fit it to the mathematical form represented in Eqn. 1. This mathematical fitting procedure is carried out in the computer using one of a number of well-established fitting routines. (It should be noted that in general more than two exponentials may in fact be contained in G(τ). However, because of the limited signal to noise ratio which results from a clinically desirable short measurement time, approximately (1-3 sec), the correlation function could be fit quite satisfactorily to Eqn. 1.) As a result of the fitting procedure, one deduces the fundamental parameters $I_f$ and $I_s$ and their sum $I_f + I_s = I_{tot}$.

It is possible to show that $I_f$ and $I_s$ can be related to one another using the following model for the origin of the slowly moving component. The actual distribution of protein species in the lens may be approximated as a simple bimodal distribution corresponding to a two state model for the distribution of protein mass. Let $N_f$ denote the number density (number per unit volume) of the small, fast diffusers, and let $N_s$ denote the number density of the large aggregates. Furthermore, let $M_f$ denote the molecular weight of the lighter species and $M_s$ the molecular weight of the aggregates. Since the aggregates are composed of the rapidly diffusing species, $(m_s/m_f)$ is the number of small proteins in each of the large aggregates. In a clear lens when no aggregation has occurred $N_s = 0$, and all the protein is regarded as existing in an unaggregated state. Under these conditions, the corresponding number density of proteins is denoted as $N_f^0$. At each point in the lens, the two state model of the formation of aggregates implies the following condition:

$$N_f^0 M_f = N_f M_f + N_s M_s. \tag{2}$$

This equation represents simply the conservation of mass. The left hand side is the total mass density of the proteins associated with both peaks of the biomodal mass distribution. $N_f M_f$ is the mass density associated with the light mass peak. $N_s M_s$ is the mass density associated with the heavy molecular weight peak in the mass distribution. Since the protein concentration is known to vary spatially within the lens, it may be expected that $N_f^0$ will be a function of spatial position inside the lens. In the normal young lens it is expected that $N_s = 0$ and $N_f = N_f^0$. With aging and early cataractogenesis, $N_f$ becomes smaller than $N_f^0$ and $N_s$ increases. If $N_f^0$ is regarded as a constant independent of age, then Eqn. (2) establishes at each time a relationship between $N_s$ and $N_f$ based on the assumption that no new protein has been produced. Of course, $N_f^0$ can increase with age. This is to be expected particularly in the cortex where protein expression continues with aging. On the other hand $N_f^0$ can be expected to be relatively independent of age in the nucleus where no gene expression is occurring.

The parameters $I_f$ and $I_s$ may be expressed in terms of $N_f$, $N_s$, $M_f$ and $M_s$. Each of the scattering elements may be regarded as being spatially distributed at random positions within the illuminated region of the lens. Under these conditions, since the size of the proteins of mass $M_f$ is approximately 100Å (i.e. small compared to the wavelength of the light), $I_f$ is proportional to the square of the mass $(M_f)$ of the scatterers and to the concentration $N_f$ of scatterers. Thus $$I_f = k_f N_f M_f^2. \tag{3a}$$

$k_f$ is a constant of proportionality independent of scattering angle, but dependent upon such quantities as the incident light intensity and polarization, the index of refraction of the protein compared to the mean index of the lens, and the geometric arrangement of the light collection optics in the QLS spectrometer.

In the case of the larger scattering element it is necessary to include the fact that the size of these objects can be comparable to the light wavelength. As a result, the intensity of light scattered from these will be a strong function of the scattering angle. Thus, $I_s$ may be written as:

$$I_s(\overline{R}_s, \theta) = k_s(\overline{R}_s, \theta) N_s M_s^2. \tag{3b}$$

In this equation, $k_s(\overline{R}_s, \theta)$, the coefficient of proportionality, is expressly designated as dependent upon scattering angle $\theta$, and the mean radius $\overline{R}_s$ of the heavy scattering element. Extensive calculations have been made regarding the form of $k_s(\overline{R}_s, \theta)$ for various shapes of dielectrics. It is important to keep in mind that the angular anisotropy in the intensity of light scattered from an aggregate whose size is comparable to the light wavelength or larger can be quite large. Studies of this anisotropy factor show that the ratio of the light intensity scattered near the forward direction to that scattered towards the backward direction can range from unity for small particles to approximately 100 for aggregates having sizes of several thousand Angstroms. The scattering angle used experimentally was approximately 135°. Thus $k_s(\overline{R}_s, \theta)$ could be as much as 100 times smaller than $k_f$ if the scatterers are as large as several thousand Angstroms in size. Of course, it is possible to select scattering angles, in principle, anywhere within the back-scattering quadrant, however, the choice of angle can significantly effect $k_s$.

While the aggregates will vary in size from approximately 200Å to approximately 1000Å, it is only necessary to consider the largest of these since they will have the greatest effect on scattering. This allows a large amount of scattering to occur even when there are very few 1000Å aggregates present. Since this scattering may be detected, it is possible to identify the existence of large aggregates even when there are very few present. Apart from these considerations, it is expected that $k_s$ will also depend on light intensity and polarization, index of refraction and light collection geometry in the same way as $k_f$.

It is now possible to establish a relationship between $I_f$ and $I_s(\overline{R}_s, \theta)$, the experimentally measured parameters. The quantity $(N_f^0 - N_f)$ represents the number density of fast component converted to aggregates. Both $I_f$ and $I_s$ can be expressed in terms of this quantity. From equation (3a) it is found that:

$$I_f = k_f [N_f^0 - (N_f^0 - N_f)] M_f^2,$$

thus $$I_f = I_f^0 - k_f M_f^2 (N_f^0 - N_f). \tag{4}$$

Here $I_f^0 = k_f N_f^0 M_f^2$ is the intensity of light scattered from the fast diffusing species in the absence of any aggregation. From Eqn. (3b) it is seen that $I_s$ is proportional $N_s$. Also, this quantity is proportional to $(N_f^0 - N_f)$ as follows from the conservation condition Eqn. (2):

$$N_s = (N_f^0 - N_f)(M_f/M_s).$$

Using this in Eqn. (3b) gives:

$$I_s(\overline{R}_s, \theta) = k_s(\overline{R}_s, \theta) M_s M_f (N_f^0 - N_f). \tag{5}$$

Equations (4) and (5) express quantitatively the reduction in $I_f$ and the increase in $I_s$ which is produced by the reduction $(N_f^0-N_f)$ in fast diffusing species and their conversion to heavy aggregates. This conversion gives a definite relationship between $I_f$ and $I_s$ which can be obtained by expressing $(N_f^0-N_f)$ in terms if $I_s$ using Eqn. (5) and substituting the results in Eqn. (4) i.e.

$$I_f = I_f^0 - \left[\frac{k_f}{k_s(R_s,\theta)}\right]\left[\frac{M_f}{M_s}\right]I_s \quad (6)$$

According to this result if $I_f$ and $I_s$ are measured in the nuclear region where $N_f^0$ remains roughly constant with age, as the aggregation proceeds a plot of the values of $I_f$ and $I_s$ measured at different times will produce a straight line with a negative slope whose magnitude is S where $$((k_f M_f/k_s(\overline{R}_s, \theta)M_s) = S. \quad (7)$$

The value of the intercept in this plot at $I_s=O$ is $I_f^0$. In general, $I_f^0$ can be expected to change with position in the lens. In the cortex where protein is being produced $I_f^0$ can be expected to change with age as well as position. The size of the fast particles can be estimated approximately 100Å while that of the large scatterers is taken to be approximately 1000Å. The ratio $(M_f/M_s)$ is approximately $(1/10)^3$ or $10^{-3}$. It is also possible to estimate from the angular disymmetry of the large aggregate that $[k_f/k_s(\pi)]$ is approximately $10^2$. Thus the quantity S may be roughly estimated as 0.1.

Since $I_{tot}=I_s+I_f$ is the total intensity of light scattered into the collection optics from the mobile scattering elements, it is possible to examine how $I_{tot}$ depends upon $I_s$ and $I_f$ separately:

$$(I_{tot})=I_f+I_s. \quad (8)$$

Using Eqn (6) in the above yields:

$$(I_{tot}) = I_f^0 + \left(1 - \left[\frac{k_f}{k_s(R_s,\theta)}\right]\left[\frac{M_f}{M_s}\right]\right)I_s. \quad (9)$$

Thus a plot of $I_{tot}$ versus $I_s$ has an intercept at $I_s=0$ of $I_f^0$, and a slope of (1-S). If the estimate of S as approximately equal to 0.1 is correct, the slope of the $I_{tot}$ versus $I_s$ graph will be somewhat less than unity. If measurements of $I_{tot}$ and $I_s$ are made at a fixed position in the lens for an ensemble of subjects at various ages and varying early stages of cataract development, the corresponding pairs of points in a graph of $I_{tot}$ versus $I_s$ are expected to fall on the straight line given by Eqn. (9). This will be true if $I_f$ is approximately the same for each subject, and if S remains at approximately 0.1 or less for each subject. On such a "universal curve" the positioning of a point along the vertical or $I_{tot}$ axis indicates the degree of formation of heavy aggregate species. If the measurements $I_s$ and $I_f$ indicate that $I_{tot}$ is approximately 20 $I_f^0$, such a state of aggregation is likely to produce a degree of turbidity quite apparent on visual observation. The great advantage of the present form of investigation is that it provides a linear and therefore, very sensitive measure of the earliest stages of the aggregation process well before such aggregation could be detected using either photographic or visual detection, through the slit lamp microscope. The precise value of $I_{tot}$ or $I_s$ as a function of time during the progression of the disease provides a very useful quantitative characterization of the development of the aggregates.

It is also possible to relate the increase in $I_{tot}$ to the decrease in $I_f$ as follows: Since $I_{tot}=I_f+I_s$, $I_s$ may be expressed in terms of $I_f$ using Eqn. (4) and Eqn. (5). This results in the following relationship between the measured quantities $I_f$ and $I_{tot}$:

$$I_f=[1/(1-S)]I_f^0-[S/(1-S)]I_{tot}. \quad (10)$$

Thus a plot of the experimental values with $I_f$ as ordinate and $I_{tot}$ as abscissa should yield a straight line whose intercept at $I_{tot}=I_f^0$ is $I_f=I_f^0$ and whose slope is negative with a magnitude $S/(1-S)$. Also $I_f=0$ when $I_{tot}=(1/S)I_f^0$. Eqn. (10) represents quantitatively the decrease in $I_f$ which results from the conversion of the lighter proteins into the heavy aggregates. The total disappearance of all the lighter proteins occurs when the total light intensity reaches a value equal to $I_f^0/S$ where S is the important parameter defined in Eqn. (7).

Experimental studies have demonstrated that the theory above does in fact describe the experimentally observed relationship between $I_{tot}$ and $I_s$ or $I_{tot}$ and $I_f$ within experimental accuracy. The experiments have provided a fundamentally important practical result shown in FIGS. 4 and 5. These figures show that a plot of $I_{tot}$ versus $I_s$ is in fact a straight line, regardless of the identity or age of the subject or the location studied along the optic axis of the lens. Thus, it is possible to label a plot of $I_{tot}$ versus $I_s$ as a universal curve. This universal curve permits a very useful method for the quantitative characterization of the degree of cataract. In an actual measurement of the photocurrent fluctuation, one determines $I_f$, $I_s$ and $I_f+I_s=I_{tot}$. One then locates the position of this point on the universal curve. The advance of cataract corresponds to movement of this point in a direction radially outward along the universal curve. A reversal of the cataractogenic process corresponds to a movement of the system point $(I_{tot}, I_s)$ towards the origin. By establishing the value of the intercept $I_{tot}(I_s=0)=I_f^0$, it is possible to construct a universal curve whose ordinate axis is $(I_{tot}/I_f^0)$ and whose abscissa is $I_s$. A lens region for which no aggregation has occurred corresponds to $(I_{tot}/I_f^0)=1$. A lens region where so much conversion to the aggregated states has occurred so that opacification is visible clinically corresponds to $(I_{tot}/I_f^0)$ equaling approximately 30. The value of the ratio $(I_{tot}/I_f^0)$ is thus a direct measure of the degree of cataractogenesis.

Figure 1:
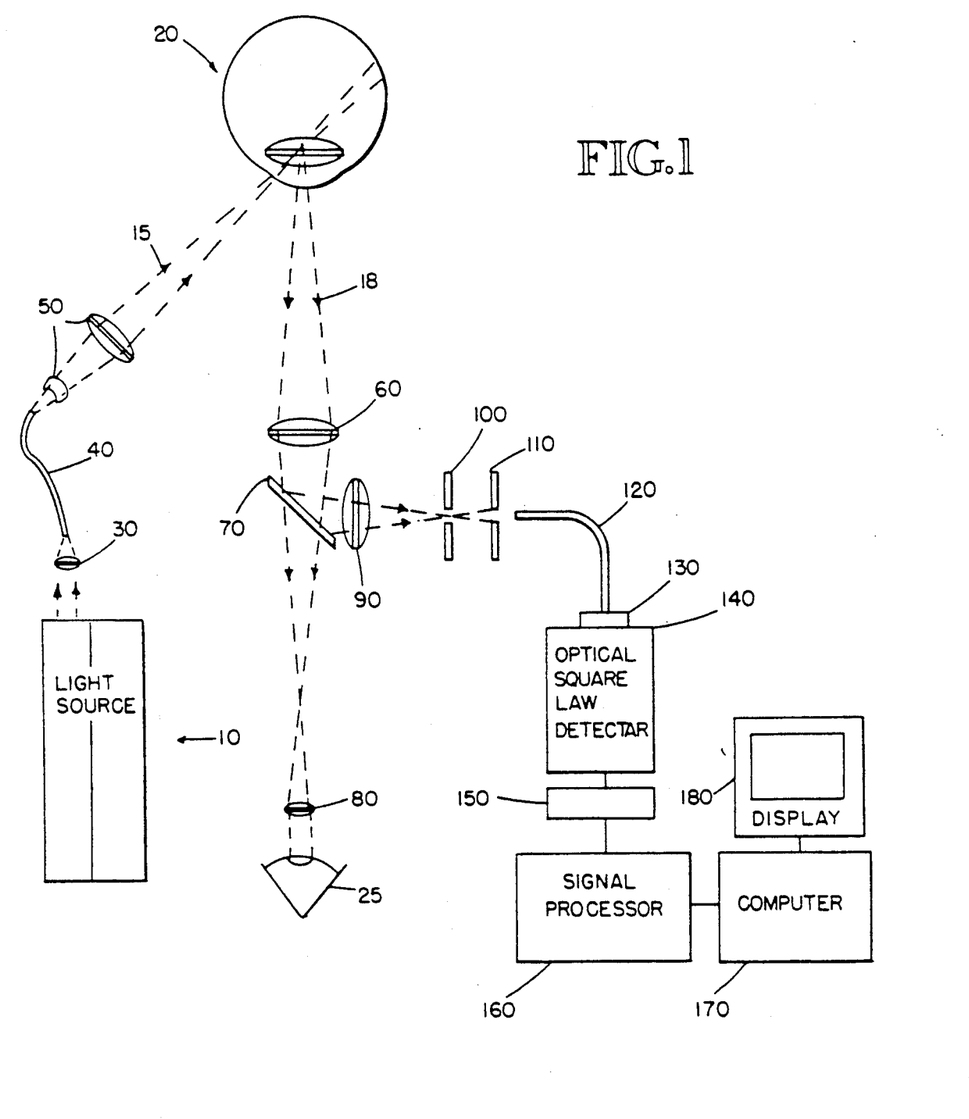
FIG. 1 is a schematic representation of an optical scattering analyzer for the study of the temporal fluctuations of laser light scattered from the lens in vivo.

Turning now to the Figures, FIG. 1 is a schematic representation of an optical scattering analyzer for the study of the temporal fluctuations of laser light scattered from the lens in vivo. In FIG. 1, a source of substantially monochromatic, coherent, collimated light 10, such as a laser, delivers a light beam 15, to the subject's eye 20, through a delivery means, which may consist of, for example, a focusing lens 30 which couples the light into a fiber optic delivery cable 40, and a set of delivery optics 50. The delivery optics serve to focus the light 15 onto the subject's eye at the specific location at which the measurement is to be taken. The light must be focussed for two reasons. First, the size of the illuminated area is inversely proportional to the coherence area of the scattered light. By focusing onto a small area, a greater coherence area is obtained which allows easier measurement. Second, the incident contact area on the lens in inversely proportional to the scattering area on the retina. Thus by focusing down on the eye lens, the light going to the retina is diffused, thereby preventing retinal damage. Scattered light 18 from the eye lens, passes through a collector such as an objective lens 60 onto a beam splitter 70. The beam splitter 70 serves to allow the observer to focus and position the incident light while measuring the scattered light. Part of the beam passes through the beam splitter 70 to an ocular lens 80, which focuses the image for the observer's eye 25. By observing the scattering in this manner, a physician can control the laser beam and position it at a specific location on the subject's eye 20. The portion of the scattered light which is reflected by the beam splitter 70 passes into a collection means which can consist of a relay lens 90 to focus the light reflected from the beam splitter 70, an aperture stop 100 to limit the length of the beam observed, a coherence angle aperture 110 to limit the number of coherence areas collected, a fiber optic collection cable 120, and an optical filter 130 to filter out any extraneous light from that to be measured. Light passing through the optical filter 130, is converted into a photoelectric signal by an optical square law detector 140, such as a photomultiplier tube or solid-state photodiode. The signal from the optical square law detector 140 is pre-processed by a preamplifier and discriminator 150. This signal is then inputted into a signal processor 160 which can be an autocorrelator or a power spectrum analyzer, and a computer 170 for processing as discussed previously. The autocorrelation function or power spectrum and any calculated parameters can be shown on a display 180.

Figure 2:
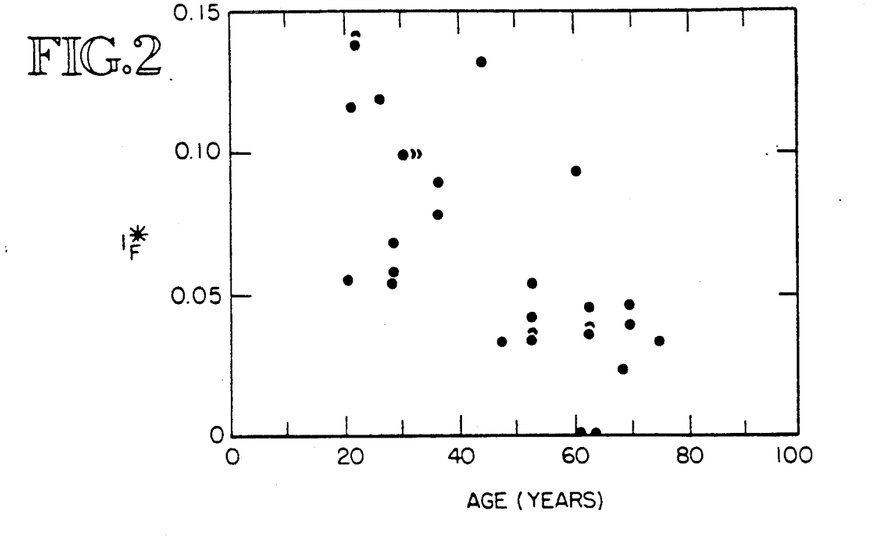
FIG. 2 is a plot of $I_f^*$ versus age at the position of the anterior nucleus in 29 subjects.

FIG. 2 is a presentation of measurements of $I_f^*$, the intensity of light scattered from the rapidly diffusing component, as a function of age as measured in the anterior nucleus in twenty-nine subjects. $I_f^*$ is obtained from the computer analysis of the correlation function and is directly proportional to $I_f$. The numerical constant relating $I_f^*$ to $I_f$ is determined entirely by instrumental gain factors. This graph shows clearly the statistically significant reduction in the concentration of this unaggregated protein as the lens nucleus ages.

The rate of diffusion $\Gamma_f$ for this component was measured and found to be $1.5 \times 10^4 \text{ sec}^{-1} < \Gamma_f < 2.5 \times 10^4 \text{sec}^{-1}$. Using these values of $I_f$ and the value $K = 2.60 \times 10^5 \text{cm}^{-1}$, the diffusion coefficient $D_f$ is found to be $2.2 \times 10^{-7} \text{ cm}^2/\text{sec} < D_f < 3.7 \times 10^{-7} \text{cm}^2/\text{sec}$. These values can be compared with the value $2.23 \times 10^{-7} \text{cm}^2/\text{sec}$ found from light scattering studies on monodisperse alpha crystallins. It is possible, therefore, to associate the rapidly diffusing species with the unassociated α-crystallin proteins in the lens cell cytoplasm. The decrease of $I_f^*$ with age is consistent with biochemical studies showing the gradual disappearance of the alpha crystalline in the aging lens nucleus.

Figure 3:
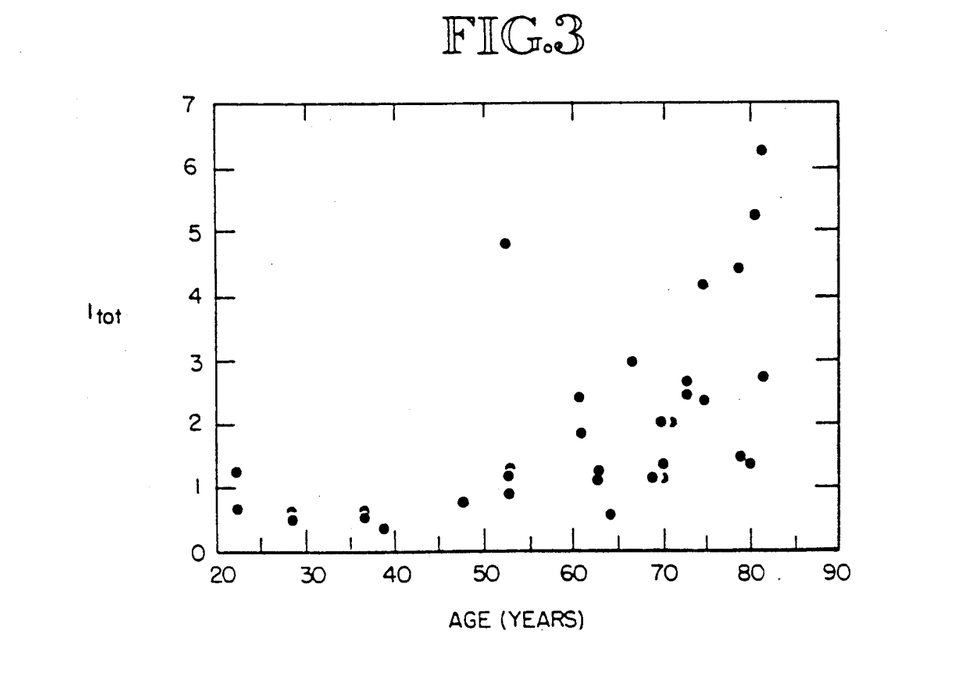
FIG. 3 is a plot of $I_{tot}$ versus age at the position of the central nucleus in 32 subjects.

In FIG. 3, $I_{tot}$ versus age for 33 persons as measured in the lens central nucleus is plotted. This graph shows that in the age group ranging from 20 to 50 years of age the scattered intensity remains relatively small. However, with aging beyond 60 years, a statistically significant increase of total scattered intensity with age is observed. This increase reflects age related development of senile nuclear cataract. The results presented in FIG. 3 are consistent with previous transmission studies done by others. This in-vivo data combined with the linear relationship between $I_{tot}$ and $I_s$ shown in FIG. 5 indicates that the development of senile cataract in the nucleus is associated with the conversion of the rapidly diffusing crystallin species to much larger slowly diffusing molecular aggregates.

Figure 4:
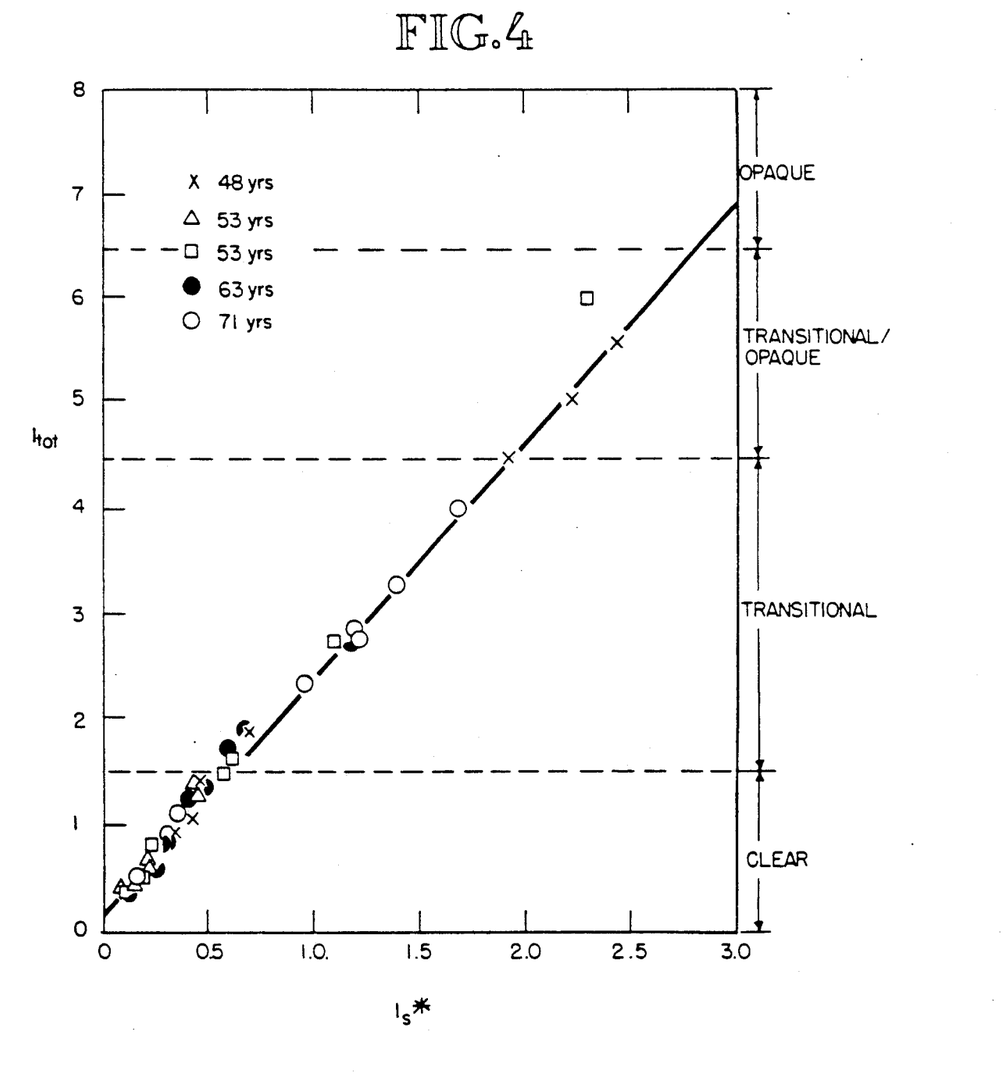
FIG. 4 is a plot of $I_{tot}$ versus $I_s^*$ for five preoperative cataract patients.

FIG. 4 represents the results of measurements made on five patients presenting preoperative lenticular opacification distributed at various locations in the lens. All the data were obtained at or near the optic axis of the lens. Typically five or six points ranging from anterior cortex to posterior nucleus were studied for each patient. The patients ranged in age from 48 to 71 years. $I_{tot}$ is plotted along the ordinate. Also, a qualitative visual designation of the degree of scattering associated with the observed values of $I_{tot}$ is indicated along this axis. On the abscissa, $I_s^*$ is plotted. $I_s^*$ is measured in the same units as $I_f^*$. As with $I_f^*$, the numerical constant relating to $I_s^*$ to $I_s$ is determined entirely by instrumental gain factors. The entire range over which $I_{tot}$ is measured corresponds to about a factor of 30 ranging from $I_{tot}$ of approximately 0.2 when $I_s^*$ is approximately 0 to $I_{tot}$ of approximately 6 when $I_s^*$ is approximately 2.6. All measurements were confined to points which did not exhibit the multiple scattering associated with opaque regions. The range of $I_{tot}$ studied corresponds to the full domain of early cataract development. This domain corresponds to a factor of about 30 in total scattered intensity, as is consistent with the previous discussion. It is also observed that in this domain of scattering $I_{tot}$ is indeed linearly proportional to $I_s$ as predicted in Eqn. (9). This linear relationship holds both for all individuals studied, and for all the points studied in the lens of a single individual. Thus, the 48 year old patient (indicated by X on the Figure) has values for $I_{tot}$ ranging from $I_{tot}$ of approximately 0.9 to $I_{tot}$ of approximately 5.5. This is a quantitativeexpression of the fact that along the optic axis of this patient's lens, there are "normal" zones in which little conversion from fast to slowly diffusing proteins has occurred. Here $0.9 \leq I_{tot} \leq 1.5$. Nevertheless, a few millimeters away, a considerable conversion to the slowly moving species has occurred. Here the light scattering is much stronger: $4.0 \leq I_{tot} \leq 5.5$. This graph clearly suggests that measurement of $I_{tot}$ and $I_s$ at a fixed position in the lens can permit a quantitative characterization of the degree of cataract development at that position. As cataractogenesis proceeds at a fixed position in the lens, $I_{tot}$ and $I_s$ will increase along the "universal curve" of $I_{tot}$ versus $I_s$. On the other hand, the decrease of $I_{tot}$ and $I_s$ along the universal curve would correspond to an increase in fast diffusing species and a reduction the amount of slowly diffusing proteins. The finding that all the data from each person and each location falls on the $I_{tot}$ versus $I_s$ line clearly suggests that this "universal curve" can provide a very sensitive, linear and quantitative characterization of the degree of the molecular changes associated with early cataract. It should be kept in mind that visual or photographic detection of early cataract is characterized by a logarithmic response and is consequently less sensitive particularly in the early stages of cataractogenesis.

Figure 5:
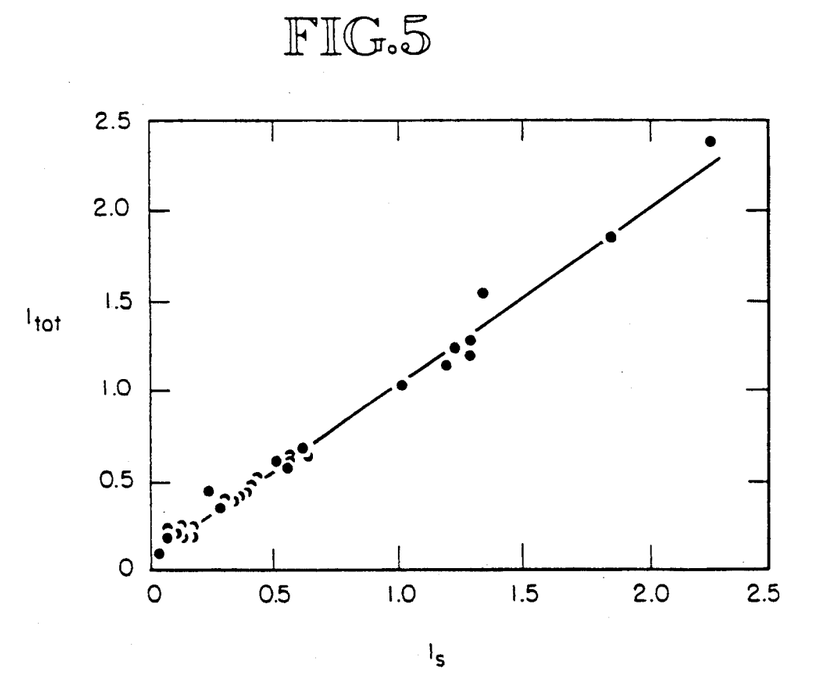
FIG. 5 is a plot of $I_{tot}$ versus $I_s$ at the position of the central nucleus in 28 subjects.

An investigation at fixed points in the lens of the slope (1-S) of the linear relationship (Eqn. 9) between $I_{tot}$ and $I_s$ was also obtained. In FIG. 5 a plot of $I_{tot}$ versus $I_s$ as observed at the central nucleus for a subgroup of 28 patients with preoperative cataracts in the age group from 23-82 years is shown. This subgroup was selected to consist of individuals having no "opaque" or "transitional-opaque" regions in the lens nucleus. In analyzing the correlation function in these experiments the same units were chosen for the measurement of $I_{tot}$ and $I_s$.

FIG. 5 showns unambiguously that in the central nucleus the relationship between $I_{tot}$ and $I_s$ is quite linear. From this graph it can be deduced that the magnitude of the slope parameter [see Eqn. 7 and 9] is given by (1-S)=(0.96±0.02). $I_f$=0.055±0.015 at the center of the lens nucleus.

Similar studies were conducted on the same population at the anterior nucleus and the posterior nucleus. Table I below lists the measurements of (1-S) and $I_f$ at each of these positions. The units for the determination of $I_s$ and $I_{tot}$ are the same and are determined by gain factors in the autocorrelation output channels. Thus the absolute magnitude of $I_f$ as listed in Table 1 is without physical significance. Nevertheless the magnitude of $I_f$ sets the scale against which cataract induced changes in $I_{tot}$ and $I_s$ are to be compared. The slope (1-S) indicates that the important dimensionless factor S as defined in Eqn. 7 has the value S=0.04±0.02. This is consistent with the previous order of magnitude estimate of 0.1 for the value for S based on the assumption that the slowly diffusing species corresponds to an element roughly 1000Å in size.

TABLE 1

Measurements of the Slope and Intercept of
the Relationship $I_{tot} = I_f + (1-S)I_s$ at
Various Positions in the Lens

| Position | Slope | $I_f$ |
|---|---|---|
| Anterior Nucleus | 0.96 ± 0.03 | 0.09 ± 0.02 |
| Central Nucleus | 0.96 ± 0.03 | 0.05 ± 0.02 |
| Posterior Nucleus | 0.95 ± 0.03 | 0.11 ± 0.03 |

EXAMPLE

The data shown in FIGS. 2-5 was obtained from a group consisting of a total of 49 individuals ranging in age from 21 to 82 years. Among these subjects nine had normal, clear lenses, and forty were pre-operative cataract patients with lenticular opacifications distributed at various locations. The results for this group are for measurements taken on the anterior cortex and three locations in the nucleus (anterior, central, posterior nucleus). All measurements were taken on or near the optical axis of the lens.

Light from a stable helium-neon laser(λ=632.8 nm) was guided through the optics of a modified Reichert slip lamp microscope to the human lens. One milliwatt was focused to a 75 micron diameter cylindrical region in the lens. Posterior to the focal region in the lens, the beam diverged so that the irradiance on the retinal tissue was approximately 0.03 watts/cm² which was two orders of magnitude below the damage threshold for the retina which is 2 watts/cm² for 10 second exposures. The light scattered from the focused incident beam within the lens was visualized easily by the operator looking through the slit lamp microscope. This aperture could be located at the desired illuminated region of the tissue using the instrument's positioning controls. A small amount of light scattered into this aperature (about 3 coherence solid angles) was conducted to a photomultiplier tube through a fiber optic cable. A measurement was activated when a button was pressed which began the processing of the scattered light signal by the autocorrelator. The resulting autocorrelation function was analyzed by an IBM-XT personal computer which was programmed to fit each correlation function to the two-component exponential form shown in Eqn. 4. After fitting each curve, the computer presented the values for $I_{tot}$, $I_f$, $I_s$, $\Gamma_f$, $\Gamma_s$ and α.

The values of α determined by the computer for the measurements were within the range 0.18±0.02. These values are close to an expected value of 0.166 which is determined from a calculation that takes into account the number of coherence solid angles, N, subtended by the pick-up aperature of the scattered light receiver: α(expected)=½N. For the aperature in the instrument N is approximately 3.

From the close correspondence between the expected and measured values of α, it can be concluded that the total scattered light is produced primarily by moving molecular components and that scattering from large, static structures is relatively small.

The autocorrelator used was a Coulter/Langely-Ford digital autocorrelator and contained 128 data channels. For each location in a subject's lens, measurements were taken at two sample times: 5 microseconds and 50 microseconds. The data were accumulated for 3 seconds for each measurement. The autocorrelation function obtained with the 5 microsecond sample time, when analyzed, provided the parameters $I_f$, $\Gamma_f$ and I(tot). The autocorrelation function obtained with the 50 microsecond sample time provided $I_s$, $\Gamma_s$ and I(tot). The apparent scattering angle (i.e. outside the eye) was 135°. Refraction at the air-cornea interface made the actual internal scattering angle slightly larger. Based on calculations, which take into account the index of refraction of the ocular tissues, the radius of curvature of the cornea, and the measurement location within the lens, it is possible to estimate that the actual scattering angle (i.e. inside the eye) was 138.5°. Using $\theta$ 138.5°, the value of the wave vector K for the scattering process was calculated to be $K=2.60\times10^5$ cm$^1$. In this calculation the value 1.40 was used for the index of refraction of the human lens.

Equivalents

Those skilled in the art will recognize, or be able to ascertain, using no more than routine experimentation, many equivalents to the specific embodiment of the invention described herein. For example, the delivery, observation, control and collection optics are not intended to be solely limited to the embodiments described herein, but rather are intended to extend to any optical system suitable for these purposes. Such equivalents are intended to be encompassed by the following claims.

We claim:

1. Apparatus for in vivo inspection of ocular tissue, comprising:
   means for producing substantially monochromatic, coherent, collimated light;
   means for focusing the light on a specific measurement location of a subject's ocular tissue;
   means for collecting the light scattered by the ocular tissue, the scattered light having an intensity subject to temporal fluctuations;
   means for producing an electrical signal representative of the temporal fluctuations;
   means for analyzing the electrical signal to measure the relative average intensity of the light scattered by slow moving protein aggregates in the ocular tissue ($I_s$) and the relative average intensity of the light scattered by fast moving protein species in the ocular tissue ($I_f$); and means for locating the position of a first member of the group of measurements consisting of $I_s$, $I_f$, and their sum $I_{tot}$ on a universal curve defined by the relationship of the first member of the group to a second member of the group, the position on the curve corresponding to the degree of cataractogenesis at the specific measurement location in the ocular tissue of the subject.

2. The apparatus of claim 1 wherein the means for producing substantially monochromatic, coherent, collimated light comprises a laser.

3. The apparatus of claim 1 wherein the first member is $I_s$ and the second member is $I_{tot}$.

4. The apparatus of claim 1 wherein the means for analyzing the electrical signal comprises:
   means for measuring the temporal fluctuations represented by the signal;
   means for calculating a power spectrum associated with the temporal fluctuations; and
   means for utilizing the power spectrum to measure $I_s$ and $I_{tot}$.

5. The apparatus of claim 4 wherein the means for producing substantially monochromatic, coherent, collimated light comprises a laser.

6. The apparatus of claim 4 wherein the means for calculating a power spectrum associated with the fluctuations is a computer.

7. The apparatus of claim 4 wherein the means for producing the electrical signal is a photomultiplier tube.

8. The apparatus of claim 4 wherein the means for focusing the light comprises a slit lamp biomicroscope.

9. The apparatus of claim 4, further comprising means for displaying the relationship of at least one member of the group consisting of $I_s$, $I_f$ and $I_{tot}$ to another member.

10. The apparatus of claim 5 wherein the means for calculating a power spectrum associated with the fluctuations is a computer.

11. The apparatus of claim 10 wherein the means for producing the electrical signal is a photomultiplier tube.

12. The apparatus of claim 11 wherein the means for focusing the light comprises a slit lamp biomicroscope.

13. The apparatus of claim 1 wherein the means for analyzing the electrical signal comprises:
   means for measuring the temporal fluctuations represented by the signal;
   means for calculating an autocorrelation function associated with the temporal fluctuations; and
   means for utilizing the autocorrelation function to measure $I_f$ and $I_s$.

14. The apparatus of claim 2 wherein the means for calculating an autocorrelation function is a computer.

15. The apparatus of claim 2 wherein the means for producing the electrical signal is a photomultiplier tube.

16. The apparatus of claim 2 wherein the means for focusing the light comprises a slit lamp biomicroscope.

17. The apparatus of claim 2, further comprising means for displaying the relationship of at least one member of the group consisting of $I_s$, $I_f$ and $I_{tot}$ to another member.

18. The apparatus of claim 13 wherein the means for producing substantially monochromatic, coherent, collimated light comprises a laser.

19. The apparatus of claim 18 wherein the means for calculating an autocorrelation function is a computer.

20. The apparatus of claim 19 wherein the means for producing the electrical signal is a photomultiplier tube.

21. The apparatus of claim 20 wherein the means for focusing the light comprises a slit lamp biomicroscope.

22. Apparatus for in vivo inspection of ocular tissue, comprising:
   means for producing substantially monochromatic, coherent, collimated light;
   means for focusing the light on a specific measurement location of a subject's ocular tissue;
   means for collecting the light scattered by the ocular tissue, the scattered light having an intensity subject to temporal fluctuations;
   an optical square law transducer for producing an electrical signal representative of the temporal fluctuations;
   means for analyzing the electrical signal to measure the relative average intensity of the light scattered by slow moving protein aggregates in the ocular tissue ($I_s$) and the relative average intensity of the light scattered by fast moving protein species in the ocular tissue ($I_f$); and
   means for locating the position of a first member of the group of measurements consisting of $I_s$, $I_f$, and their sum $I_{tot}$ on a universal curve defined by the relationship of the first member of the group to a second member of the group, the position on the curve corresponding to the degree of cataractogenesis at the specific measurement location in the ocular tissue of the subject.

23. The apparatus of claim 22 wherein the means for analyzing the electrical signal comprises:
   means for measuring the temporal fluctuations represented by the signal;
   means for calculating an autocorrelation function associated with the temporal fluctuations; and
   means for utilizing the autocorrelation function to measure $I_f$ and $I_s$.

24. The apparatus of claim 22 wherein the means for analyzing the electrical signal comprises:
   mean for measuring the temporal fluctuations represented by the signal;
   means for calculating a power spectrum associated with the temporal fluctuations; and
   means for utilizing the power spectrum to measure $I_s$ and $I_{tot}$.

25. The apparatus of claim 22 wherein the means for producing substantially monochromatic, coherent, collimated light comprises a laser.

26. The apparatus of claim 22 wherein the optical square law transducer is a photomultiplier tube.

27. The apparatus of claim 22 wherein the optical square law transducer is a solid-state photodiode.

28. The apparatus of claim 22 wherein the means for focusing the light comprises a slit lamp biomicroscope.

29. The apparatus of claim 22 wherein the first member is $I_s$ and the second member is $I_{tot}$.

30. The apparatus of claim 25 wherein the means for producing substantially monochromatic, coherent, collimated light provides approximately one milliwatt of light power.

31. The apparatus of claim 24 wherein the means for calculating a power spectrum associated with the fluctuations is a computer.

32. The apparatus of claim 24, further comprising means for displaying the relationship of $I_s$ and $I_{tot}$.

33. The apparatus of claim 23 wherein the means for calculating an autocorrelation function is a computer.

34. The apparatus of claim 23, further comprising means for displaying the relationship of at least one member of the group consisting of $I_s$, $I_f$ and $I_{tot}$ to another member.

35. Apparatus of in vivo inspection of ocular tissue, comprising:
    means for producing substantially monochromatic, coherent, collimated light;
    means for focusing the light on a specific measurement location of a subject's ocular tissue;
    means for collecting the light scattered by the ocular tissue, the scattered light having an intensity subject to temporal fluctuations;
    an optical square law transducer for producing an electrical signal representative of the temporal fluctuations;
    means for analyzing the electrical signal to measure the relative average intensity of the light scattered by slow moving protein aggregates in the ocular tissue ($I_s$) and the relative average intensity of the light scattered by fast moving protein species in the ocular tissue ($I_f$);
    means for providing at least two members of a group of measurements consisting of $I_s$, $I_f$, and their sum, $I_{tot}$, from each of a plurality of subjects; and
    means for using the measurements from each of the plurality of subjects to produce a universal curve defined by the relationship of one member of the group to another member of the group, wherein a position of a measurement taken in the ocular tissue of a particular subject on the universal curve corresponds to the degree of cataractogenesis at the particular measurement location in the ocular tissue of the particular subject.

36. The apparatus of claim 35 wherein the means for producing substantially monochromatic, coherent, collimated light comprises a laser.

37. The apparatus of claim 35 wherein the means for analyzing the electrical signal comprises:
    means for measuring the temporal fluctuations represented by the signal;
    means for calculating an autocorrelation function associated with the temporal fluctuations; and
    means for utilizing the autocorrelation function to measure $I_f$ and $I_s$.

38. The apparatus of claim 37 wherein the means for calculating an autocorrelation function is a computer.

39. The apparatus of claim 37, further comprising means for displaying the relationship of at least one member of the group consisting of $I_s$, $I_f$ and $I_{tot}$ to another member.

40. The apparatus of claim 37 wherein the means for producing substantially monochromatic, coherent, collimated light comprises a laser.

41. The apparatus of claim 40 wherein the means for producing substantially monochromatic, coherent, collimated light provides approximately one milliwatt of light power.

42. The apparatus of claim 35 wherein the means for analyzing the electrical signal comprises:
    means for measuring the temporal fluctuations represented by the signal;
    means for calculating a power spectrum associated with the temporal fluctuations; and
    means for utilizing the power spectrum to measure $I_s$ and $I_{tot}$.

43. The apparatus of claim 42 wherein the means for calculating a power spectrum associated with the fluctuations is a computer.

44. The apparatus of claim 42, further comprising means for displaying the relationship of $I_s$ and $I_{tot}$.

45. The apparatus of claim 35 wherein the optical square law transducer is a photomultiplier tube.

46. The apparatus of claim 35 wherein the optical square law transducer is a solid-state photodiode.

47. The apparatus of claim 35 wherein the means for focusing the light comprises a slit lamp biomicroscope.

48. The apparatus of claim 35 wherein the first member is $I_s$ and the second member is $I_{tot}$.

49. Apparatus for in vivo inspection of ocular tissue, comprising:
    means for producing substantially monochromatic, coherent, collimated light;
    means for focusing the light on a specific measurement location of a subject's ocular tissue;
    means for collecting the light scattered by the ocular tissue, the scattered light having an intensity subject to temporal fluctuations;
    means for producing an electrical signal representative of the temporal fluctuations;
    means for analyzing the electrical signal to measure the relative average intensity of the light scattered by slow moving protein aggregates in the ocular tissue ($I_s$) and the relative average intensity of the total light ($I_{tot}$) scattered by the sum of both fast moving protein species and the slow moving protein species in the ocular tissue; and
    means for locating the position of the point designated by ($I_s$, $I_{tot}$) on a universal curve defined by the relationship of $_{tot}$ to $I_s$, the position on the curve corresponding to the degree of cataractogenesis at the specific measurement location in the ocular tissue of the subject.

50. The apparatus of claim 49 wherein the means for analyzing the electrical signal comprises:
    means for measuring the temporal fluctuations represented by the signal;
    means for calculating an autocorrelation function associated with the temporal fluctuations; and
    means for utilizing the autocorrelation function to measure $I_f$ and $I_s$.

51. The apparatus of claim 50 wherein the means for producing substantially monochromatic, coherent, collimated light comprises a laser.

52. The apparatus of claim 51 wherein the means for calculating an autocorrelation function is a computer.

53. The apparatus of claim 52 wherein the optical square law transducer is a photomultiplier tube.

54. The apparatus of claim 53 wherein the means for focusing the light comprises a slit lamp biomicroscope.

55. The apparatus of claim 50 wherein the means for calculating an autocorrelation function is a computer.

56. The apparatus of claim 50 wherein the means for producing the electrical signal is a photomultiplier tube.

57. The apparatus of claim 50 wherein the means for focusing the light comprises a slit lamp biomicroscope.

58. The apparatus of claim 50, further comprising means for displaying the relationship of at least one member of the group consisting of $I_s$, $I_f$ and $I_{tot}$ to another member.

59. The apparatus of claim 49 wherein the means for producing substantially monochromatic, coherent, collimated light comprises a laser.

* * * * *

UNITED STATES PATENT AND TRADEMARK OFFICE
CERTIFICATE OF CORRECTION

PATENT NO. : 5,072,731

DATED : December 17, 1991

INVENTOR(S) : Victor G. Taratuta, et al

It is certified that error appears in the above-identified patent and that said Letters Patent is hereby corrected as shown below:

Column 14, line 37, delete "mean" and substitute therefore --means--.

Signed and Sealed this

Twenty-seventh Day of April, 1993

Attest:

MICHAEL K. KIRK

*Attesting Officer*   *Acting Commissioner of Patents and Trademarks*

UNITED STATES PATENT AND TRADEMARK OFFICE
CERTIFICATE OF CORRECTION

PATENT NO. : 5,072,731
DATED : December 17, 1991
INVENTOR(S) : Victor G. Taratuta, et. al.

It is certified that error appears in the above-indentified patent and that said Letters Patent is hereby corrected as shown below:

Column 14, claim 24, line 37, delete "mean" and substitute therefor-- means--.

Signed and Sealed this

Twenty-second Day of February, 1994

Attest:

BRUCE LEHMAN

*Attesting Officer*    *Commissioner of Patents and Trademarks*